(12) United States Patent
Deaton, Jr. et al.

(10) Patent No.: US 10,307,823 B1
(45) Date of Patent: Jun. 4, 2019

(54) METHODS AND SYSTEMS FOR REPAIRING POWDER CONTAINMENT STRUCTURES

(71) Applicant: General Electric Company, Schenectady, NY (US)

(72) Inventors: John Broddus Deaton, Jr., Niskayuna, NY (US); Thomas Charles Adcock, Glenville, NY (US); William Monaghan, Charlton, NY (US); John Joseph Madelone, Jr., South Glen Falls, NY (US); Michael Evans Graham, Slingerlands, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/810,908

(22) Filed: Nov. 13, 2017

(51) Int. Cl.
*B22F 3/105* (2006.01)
*G01N 21/88* (2006.01)
*B33Y 10/00* (2015.01)

(52) U.S. Cl.
CPC .... *B22F 3/1055* (2013.01); *B22F 2003/1058* (2013.01); *B33Y 10/00* (2014.12); *G01N 21/8851* (2013.01); *G01N 2021/8854* (2013.01)

(58) Field of Classification Search
CPC ............. B22F 3/105; B22F 3/1055; B22F 2003/1058; B33Y 10/00; B33Y 30/00; B33Y 50/02; G01N 2021/8854; G01N 21/8851; B23K 26/342
See application file for complete search history.

(56) References Cited

U.S. PATENT DOCUMENTS

| 7,047,098 | B2 | 5/2006 | Lindemann et al. |
| 8,021,138 | B2 | 9/2011 | Green |
| 9,352,413 | B2 | 5/2016 | Bruck et al. |
| 9,352,419 | B2 | 5/2016 | Bruck et al. |
| 9,505,172 | B2 | 11/2016 | Ljungblad |
| 9,522,426 | B2 | 12/2016 | Das et al. |
| 9,682,166 | B2 | 6/2017 | Watanabe |
| 9,776,282 | B2 | 10/2017 | Subramanian et al. |
| 2002/0195747 | A1 | 12/2002 | Hull et al. |
| 2011/0278773 | A1 | 11/2011 | Bokodi et al. |
| 2014/0099476 | A1 | 4/2014 | Subramanian et al. |
| 2015/0202686 | A1 | 7/2015 | Wimpenny et al. |
| 2015/0336331 | A1 | 11/2015 | Potter |
| 2016/0184893 | A1 | 6/2016 | Dave et al. |

(Continued)

FOREIGN PATENT DOCUMENTS

JP 4314414 B2 8/2009

OTHER PUBLICATIONS

International Search Report and Written Opinion, dated Jan. 28, 2019, for related International application No. PCT/US2018/055859 (13 pgs.).

*Primary Examiner* — Jamil Ahmed
(74) *Attorney, Agent, or Firm* — Armstrong Teasdale LLP (57) ABSTRACT

A method for repairing a structure in an additive manufacturing system is provided. The method includes detecting a defect in a structure formed using an additive manufacturing process, the structure including a first surface that faces a powder containing region and a second surface that faces a substantially powder free region, generating a supplemental scan path that covers at least a portion of the structure based on a location of the detected defect, and controlling a consolidation device, based on the supplemental scan path, to remedy the defect.

20 Claims, 7 Drawing Sheets

(56) References Cited

U.S. PATENT DOCUMENTS

| | | |
|---|---|---|
| 2016/0275670 A1* | 9/2016 | Ladewig .............. G06K 9/2054 |
| 2017/0120335 A1 | 5/2017 | Demuth et al. |
| 2017/0144250 A1 | 5/2017 | Gold et al. |
| 2017/0246810 A1 | 8/2017 | Gold |
| 2017/0252805 A1 | 9/2017 | Gillespie et al. |

\* cited by examiner

METHODS AND SYSTEMS FOR REPAIRING POWDER CONTAINMENT STRUCTURES

BACKGROUND

The subject matter described herein relates generally to additive manufacturing systems and, more particularly, to additive manufacturing systems including powder containment walls.

Additive manufacturing systems are essential to the production of many modern specialized components. Specifically, Selective Laser Melting (SLM) has become an essential tool for manufacturers to model and mold metal components that would otherwise be prohibitively expensive or impossible to replicate under standard metal working techniques. However, traditionally Selective Laser Melting has required a fixed container volume irrespective of the size of the component to be manufactured. As a result, the same quantity of build material is required no matter what the size of the component is. Thus, at least some have sought to make the technique more cost effective by engineering methods to minimize the building material necessary to mold a specific component. Such resource minimization techniques include constructing structures alongside the primary components to restrict the amount of powder necessary per build. However, in order to reduce the required powder necessary per build, such structures inherently require the absence of the build material on one side of their structure. This asymmetrical distribution of build material means that such structures are often susceptible to stability and structural integrity issues. Furthermore, repairing such structures can be expensive, time consuming, and result in material contamination of the build environment.

BRIEF DESCRIPTION

In one aspect, an additive manufacturing method is provided. The additive manufacturing method includes detecting a defect in a structure formed using an additive manufacturing process, the structure including a first surface that faces a powder containing region and a second surface that faces a substantially powder free region, generating a supplemental scan path that covers at least a portion of the structure based on a location of the detected defect, and controlling a consolidation device, based on the supplemental scan path, to remedy the defect.

In another aspect, an additive manufacturing system is provided. The additive manufacturing system includes a consolidation device, a powder bed, and a controller. The controller includes a processing device and a memory device. The controller is configured to generate a supplemental scan path based on the location a detected defect in a structure formed using an additive manufacturing process, the structure including a first surface that faces a powder containing region and a second surface that faces a substantially powder free region. The controller is further configured to control said consolidation device, based on the supplemental scan path, to remedy the defect.

In yet another aspect, a controller for controlling an additive manufacturing system is provided. The controller includes a memory device, a user input interface, and a processing device. The processing device is configured to generate a supplemental scan path based on the location a detected defect in a structure formed using an additive manufacturing process, the structure including a first surface that faces a powder containing region and a second surface that faces a substantially powder free region. The controller is further configured to control said consolidation device, based on the supplemental scan path, to remedy the defect.

DRAWINGS

These and other features, aspects, and advantages of the present disclosure will become better understood when the following detailed description is read with reference to the accompanying drawings in which like characters represent like parts throughout the drawings, wherein.

Unless otherwise indicated, the drawings provided herein are meant to illustrate features of embodiments of the disclosure. These features are believed to be applicable in a wide variety of systems comprising one or more embodiments of the disclosure. As such, the drawings are not meant to include all conventional features known by those of ordinary skill in the art to be required for the practice of the embodiments disclosed herein.

DETAILED DESCRIPTION

In the following specification and the claims, reference will be made to a number of terms, which shall be defined to have the following meanings.

The singular forms "a", "an", and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "substantially," and "approximately," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

As used herein, the terms "processor" and "computer," and related terms, e.g., "processing device," "computing device," and "controller" are not limited to just those integrated circuits referred to in the art as a computer, but broadly refers to a microcontroller, a microcomputer, a programmable logic controller (PLC), and application specific integrated circuit, and other programmable circuits, and these terms are used interchangeably herein. In the embodiments described herein, memory may include, but it not limited to, a computer-readable medium, such as a random access memory (RAM), a computer-readable non-volatile medium, such as a flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Further, as used herein, the terms "software" and "firmware" are interchangeable, and include any computer program storage in memory for execution by personal computers, workstations, clients, and servers.

As used herein, the term "non-transitory computer-readable media" is intended to be representative of any tangible computer-based device implemented in any method of technology for short-term and long-term storage of information, such as, computer-readable instructions, data structures, program modules and sub-modules, or other data in any device. Therefore, the methods described herein may be encoded as executable instructions embodied in a tangible, non-transitory, computer-readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including without limitation, volatile and non-volatile media, and removable and non-removable media such as firmware, physical and virtual storage, CD-ROMS, DVDs, and any other digital source such as a network or the Internet, as well as yet to be developed digital means, with the sole exception being transitory, propagating signal.

Furthermore, as used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

As used herein, the term "build cycle" refers to one cycle of an additive manufacturing process beginning with depositing powder in a powder bed and ending with removing the completed component from the powder bed.

Additionally, as used herein, the term "partially surrounds" refers to a structure (e.g., a powder containment wall) being located relative to a component such that the structure is capable of substantially containing a volume of powder located around the component. In other words, the structure may partially surround the component if the structure is sufficient to contain a volume of powder around the component. For example, if the structure is a continuous closed shape that encloses a volume, and the component is disposed within that volume, such a structure would surround the component. Alternatively, the structure may also "partially surround" the component, as that term is used in this application, in the embodiment where the structure does not entirely surround the component. A structure substantially contains a volume of powder around the component wherein the powder surrounding the component is lost at a rate less than new powder is able to be deposited.

As used herein, the term "powder" refers to any material capable of constituting the base material in an additive manufacturing system from which the finished component is formed. This may include, but is not limited to, polymers, plastics, metals, ceramics, sand, glass, waxes, fibers, biological matter, composites, and hybrids of these materials. Furthermore, use of the term "powder" should not be interpreted as limiting the consistency of the material beyond referring to the fact that the material is capable of being consolidated by a consolidation device and of substantially filling a volume between a structure and component.

As used herein, the term "substantially powder free region" refers to any portion of a build platform wherein the amount of powder deposited thereon is insubstantial enough that it is not intended to be used in a build cycle of an additive manufacturing process. In other words, a substantially powder free region of a build platform may contain any amount of powder resulting from spill over of powder over the structure or any portion of powder lost through a defect in the structure. However, a substantially powder free region does not contain a quantity of powder large enough that it is intended to be used in a build cycle of an additive manufacturing process. Specifically, a substantially powder free region may not contain a quantity of powder intended to be consolidated by a consolidation device to form a component in an additive manufacturing process.

The systems and methods described herein include detecting a defect in a structure formed using an additive manufacturing process, the structure including a first surface that faces a powder containing region and a second surface that faces a substantially powder free region, generating a supplemental scan path that covers at least a portion of the structure based on a location of the detected defect, and controlling a consolidation device, based on the supplemental scan path, to remedy the defect Additive manufacturing processes and systems include, for example, and without limitation, vat photopolymerization, powder bed fusion, binder jetting, material jetting, sheet lamination, material extrusion, directed energy deposition and hybrid systems. These processes and systems include, for example, and without limitation, SLA—Stereolithography Apparatus, DLP—Digital Light Processing, 3SP—Scan, Spin, and Selectively Photocure, CLIP—Continuous Liquid Interface Production, SLS—Selective Laser Sintering, DMLS—Direct Metal Laser Sintering, SLM—Selective Laser Melting, EBM—Electron Beam Melting, SHS—Selective Heat Sintering, MJF—Multi-Jet Fusion, 3D Printing, Voxeljet, Polyjet, SCP—Smooth Curvatures Printing, MJM—Multi-Jet Modeling Proj et, LOM—Laminated Object Manufacture, SDL—Selective Deposition Lamination, UAM—Ultrasonic Additive Manufacturing, FFF—Fused Filament Fabrication, FDM—Fused Deposition Modeling, LMD—Laser Metal Deposition, LENS—Laser Engineered Net Shaping, DMD—Direct Metal Deposition, Hybrid Systems, and combinations of these processes and systems. These processes and systems may employ, for example, and without limitation, all forms of electromagnetic radiation, heating, sintering, melting, curing, binding, consolidating, pressing, embedding, and combinations thereof.

Additive manufacturing processes and systems employ materials including, for example, and without limitation, polymers, plastics, metals, ceramics, sand, glass, waxes, fibers, biological matter, composites, and hybrids of these materials. These materials may be used in these processes and systems in a variety of forms as appropriate for a given material and the process or system, including, for example, and without limitation, as liquids, solids, powders, sheets, foils, tapes, filaments, pellets, liquids, slurries, wires, atomized, pastes, and combinations of these forms.

Figure 1:
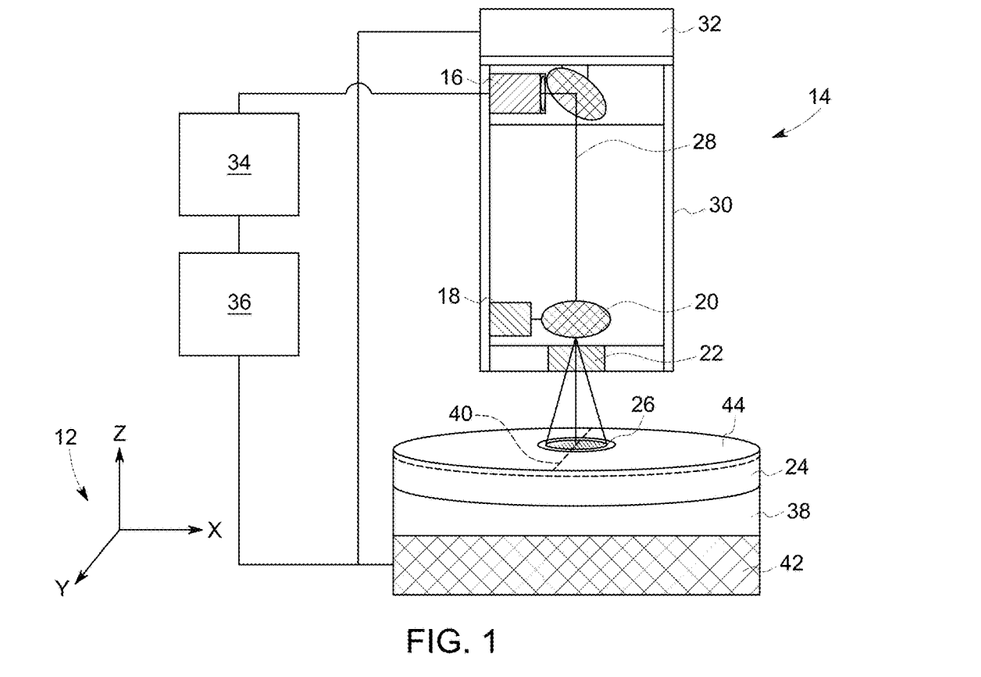
FIG. 1 is a schematic view of an exemplary additive manufacturing system 10.

FIG. 1 is a schematic view of an exemplary additive manufacturing system 10. A coordinate system 12 includes an x-axis, a y-axis, and a z-axis. In the exemplary embodiment, additive manufacturing system 10 includes a consolidating device 14 including a laser device 16, a scanning motor 18, a scanning mirror 20, and a scanning lens 22 for fabricating a component 24 using a layer-by-layer manufacturing process. Alternatively, consolidating device 14 may include any component that facilitates consolidation of a material using any of the processes and systems described herein. Laser device 16 provides a high-intensity heat source configured to generate a melt pool 26 (not shown to scale) in a powdered material using an energy beam 28. Laser device 16 is contained within a housing 30 that is coupled to a mounting system 32. Additive manufacturing system 10 also includes a computer control system, or controller 34. Mounting system 32 is moved by an actuator or an actuator system 36 that is configured to move mounting system 32 in an XY plane to cooperate with scanning mirror 20 to facilitate fabricating a layer of component 24 within additive manufacturing system 10. For example, and without limitation, mounting system 32 is pivoted about a central point, moved in a linear path, a curved path, and/or rotated to cover a portion of the powder on a powder bed 38 to facilitate directing energy beam 28 along the surface of component 24. Alternatively, housing 30 and energy beam 28 are moved in any orientation and manner that enables additive manufacturing system 10 to function as described herein.

Scanning motor 18 is controlled by controller 34 and is configured to move mirror 20 such that energy beam 28 is reflected to be incident along a predetermined path along powder bed 38, such as, for example, and without limitation, a linear and/or rotational scan path 40. In the exemplary embodiment, the combination of scanning motor 18 and scanning mirror 20 forms a two-dimension scan galvanometer. Alternatively, scanning motor 18 and scanning mirror 20 may include a three-dimension (3D) scan galvanometer, dynamic focusing galvanometer, and/or any other method that may be used to deflect energy beam 28 of laser device 16.

In the exemplary embodiment, powder bed 38 is mounted to a support structure 42, which is moved by actuator system 36. As described above with respect to mounting system 32, actuator system 36 is also configured to move support structure 42 in a Z direction (i.e., normal to a top surface of powder bed 38). In some embodiments, actuator system 36 is also configured to move support structure 42 in the XY plane. For example, and without limitation, in an alternative embodiment where housing 30 is stationary, actuator system 36 moves support structure 42 in the XY plane to cooperate with scanning motor 18 and scanning mirror 20 to direct energy beam 28 of laser device 16 along scan path 40 about powder bed 38. In the exemplary embodiment, actuator system 36 includes, for example, and without limitation, a linear motor(s), a hydraulic and/or pneumatic piston(s), a screw drive mechanism(s), and/or a conveyor system.

In the exemplary embodiment, additive manufacturing system 10 is operated to fabricate component 24 from a computer modeled representation of the 3D geometry of component 24. The computer modeled representation may be produced in a computer aided design (CAD) or similar file. The CAD file of component 24 is converted into a layer-by-layer format that includes a plurality of build parameters for each layer of component 24, for example, build layer 44 of component 24. In the exemplary embodiment, component 24 is modeled in a desired orientation relative to the origin of the coordinate system used in additive manufacturing system 10. The geometry of component 24 is sliced into a stack of layers of a desired thickness, such that the geometry of each layer is an outline of the cross-section through component 24 at that particular layer location. Scan paths 40 are generated across the geometry of a respective layer. The build parameters are applied along scan path 40 to fabricate that layer of component 24 from the material used to construct component 24. The steps are repeated for each respective layer of component 24 geometry. Once the process is completed, an electronic computer build file (or files) or scan path data set is generated, including all of the layers. The build file or scan path data set is loaded into controller 34 of additive manufacturing system 10 to control the system during fabrication of each layer.

After the build file or scan path data set is loaded into controller 34, additive manufacturing system 10 is operated to generate component 24 by implementing the layer-by-layer manufacturing process, such as a selective laser melting method. The exemplary layer-by-layer additive manufacturing process does not use a pre-existing article as the precursor to the final component, rather the process produces component 24 from a raw material in a configurable form, such as a powder. For example, and without limitation, a steel component can be additively manufactured using a steel powder. Additive manufacturing system 10 enables fabrication of components, such as component 24, using a broad range of materials, for example, and without limitation, metals, ceramics, glass, and polymers.

Figure 2:
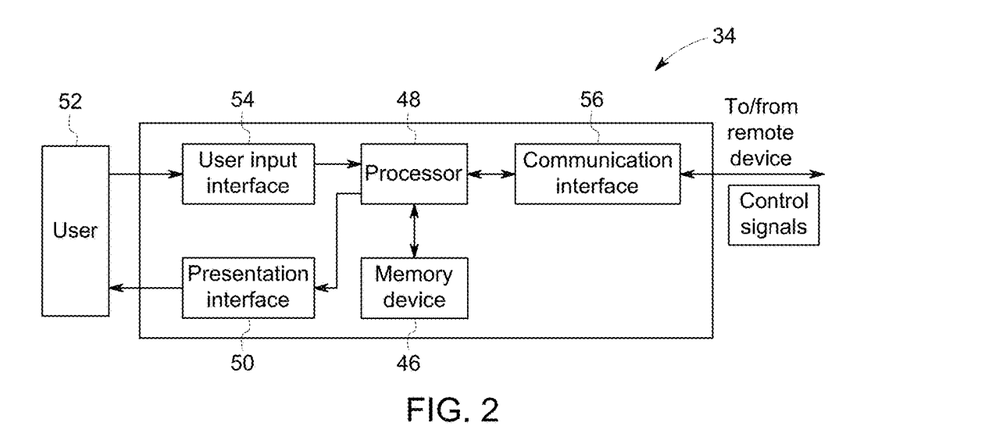
FIG. 2 is a block diagram of a controller that is used to operate the additive manufacturing system shown in FIG. 1.

FIG. 2 is a block diagram of controller 34 that is used to operate additive manufacturing system 10 (shown in FIG. 1). In the exemplary embodiment, controller 34 is any type of controller typically provided by a manufacturer of additive manufacturing system 10 to control operation of additive manufacturing system 10. In the exemplary embodiment, controller 34 executes operations to control the operation of additive manufacturing system 10 based at least partially on instructions from human operators. In alternative embodiments, controller 34 automatically executes operations to control the operation of additive manufacturing system 10. Controller 34 includes, for example, a 3D model of component 24 to be fabricated by additive manufacturing system 10. Operations executed by controller 34 include controlling power output of laser device 16 (shown in FIG. 1) and adjusting mounting system 32 and/or support structure 42, via actuator system 36 (all shown in FIG. 1) to control the scanning velocity of energy beam 28. Controller 34 is also configured to control scanning motor 18 to direct scanning mirror 20 to further control the scanning velocity of energy beam 28 within additive manufacturing system 10.

In alternative embodiments, controller 34 may execute any operation that enables additive manufacturing system 10 to function as described herein.

In the exemplary embodiment, controller 34 includes a memory device 46 and a processor 48 coupled to memory device 46. Processor 48 may include one or more processing units, such as, without limitation, a multi-core configuration. Processor 48 is any type of processor that permits controller 34 to operate as described herein. In some embodiments, executable instructions are stored in memory device 46. Controller 34 is configurable to perform one or more operations described herein by programming processor 48. For example, processor 48 may be programmed by encoding an operation as one or more executable instructions and providing the executable instructions in memory device 46. In the exemplary embodiment, memory device 46 is one or more devices that enable storage and retrieval of information such as executable instructions or other data. Memory device 46 may include one or more computer readable media, such as, without limitation, random access memory (RAM), dynamic RAM, static RAM, a solid-state disk, a hard disk, read-only memory (ROM), erasable programmable ROM, electrically erasable programmable ROM, or non-volatile RAM memory. The above memory types are exemplary only, and are thus not limiting as to the types of memory usable for storage of a computer program.

Memory device 46 may be configured to store any type of data, including, without limitation, build parameters associated with component 24. In some embodiments, processor 48 removes or "purges" data from memory device 46 based on the age of the data. For example, processor 48 may overwrite previously recorded and stored data associated with a subsequent time or event. In addition, or alternatively, processor 48 may remove data that exceeds a predetermined time interval. In addition, memory device 46 includes, without limitation, sufficient data, algorithms, and commands to facilitate monitoring of build parameters and the geometric conditions of component 24 being fabricated by additive manufacturing system 10.

In some embodiments, controller 34 includes a presentation interface 50 coupled to processor 48. Presentation interface 50 presents information, such as the operating conditions of additive manufacturing system 10, to a user 52. In one embodiment, presentation interface 50 includes a display adapter (not shown) coupled to a display device (not shown), such as a cathode ray tube (CRT), a liquid crystal display (LCD), an organic LED (OLED) display, or an "electronic ink" display. In some embodiments, presentation interface 50 includes one or more display devices. In addition, or alternatively, presentation interface 50 includes an audio output device (not shown), for example, without limitation, an audio adapter or a speaker (not shown).

In some embodiments, controller 34 includes a user input interface 54. In the exemplary embodiment, user input interface 54 is coupled to processor 48 and receives input from user 52. User input interface 54 may include, for example, without limitation, a keyboard, a pointing device, a mouse, a stylus, a touch sensitive panel, such as, without limitation, a touch pad or a touch screen, and/or an audio input interface, such as, without limitation, a microphone. A single component, such as a touch screen, may function as both a display device of presentation interface 50 and user input interface 54.

In the exemplary embodiment, a communication interface 56 is coupled to processor 48 and is configured to be coupled in communication with one or more other devices, such as laser device 16, and to perform input and output operations with respect to such devices while performing as an input channel. For example, communication interface 56 may include, without limitation, a wired network adapter, a wireless network adapter, a mobile telecommunications adapter, a serial communication adapter, or a parallel communication adapter. Communication interface 56 may receive a data signal from or transmit a data signal to one or more remote devices. For example, in some embodiments, communication interface 56 of controller 34 may transmit/receive a data signal to/from actuator system 36.

Presentation interface 50 and communication interface 56 are both capable of providing information suitable for use with the methods described herein, such as, providing information to user 52 or processor 48. Accordingly, presentation interface 50 and communication interface 56 may be referred to as output devices. Similarly, user input interface 54 and communication interface 56 are capable of receiving information suitable for use with the methods described herein and may be referred to as input devices.

Figure 3:
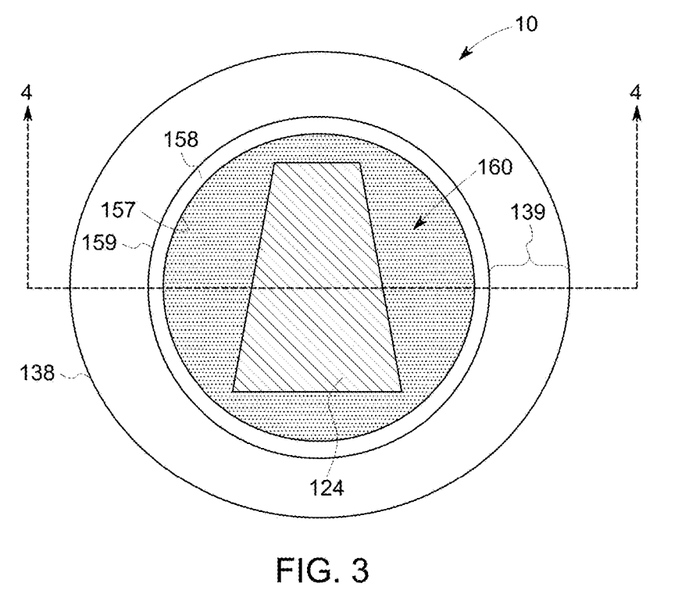
FIG. 3 is a plan schematic view of the powder bed of an additive manufacturing system including a structure and a component.

FIG. 3 is a plan schematic view of a powder bed 138 of additive manufacturing system 10 including a structure 158 and a component 124. In the exemplary embodiment, structure 158 includes a first surface 157 facing a powder containing region 137 and a second surface 159 facing a substantially powder free region 139. Specifically, in the exemplary embodiment, powder 160 is only deposited in a portion of powder bed 138 such that there is a substantially powder free region 139 of the powder bed 138. In the exemplary embodiment, substantially powder free region 139 of powder bed 138 contains substantially no powder 160. In alternative embodiments, substantially powder free region 139 may include a relatively low amount of powder 160 resulting from a portion of powder 160 spilled over from structure 158. In further alternative embodiments, substantially powder free region 139 may include any amount of powder 160 insubstantial enough to be used in the build cycle of an additive manufacturing process. In the exemplary embodiment, structure 158 is a powder containment wall. In alternative embodiments, structure 158 may include the component 124 or a portion of the component 124. In other words, in alternative embodiments, structure 158 may be an outer surface of component 124 such that the component 124 is configured to contain powder 160 within itself during a build cycle of an additive manufacturing process. In further alternative embodiments, structure 158 may be any structure used in an additive manufacturing process which includes first surface 157 that faces powder containing region 137 and second surface 159 that faces substantially powder free region 139.

In the exemplary embodiment, the build file or scan path data set received by controller 34 includes a first scan path for forming component 124, and a second scan path for forming structure 158. In alternative embodiments, the controller 34 may receive the first and second scan path through means other than a build file or scan path data set. For example, in alternative embodiments, controller 34 may receive the first and second scan paths through user input interface 54. In the exemplary embodiment, structure 158 is formed alongside component 124. In other words, in the exemplary embodiment, the laser (not shown in FIG. 3) is controlled to consolidate a layer of powder 160 along the first scan path to form component 124 and the laser is controlled to consolidate a layer of powder 160 along the second scan path to form structure 158. In alternative embodiments, structure 158 and component 124 may be formed in different cross-sections from one another.

Both structure 158 and component 124 are disposed within powder bed 138. In the exemplary embodiment, structure 158 and component 124 are separated by powder 160. However, in alternative embodiments, structure 158 may be in contact with component 124 if it is desired that structure 158 be consolidated with the part. In further alternative embodiments, structure 158 is positioned at any suitable distance from component 124 to prevent consolidating structure 158 with component 124. In the exemplary embodiment, powder 160 is a steel powder. However, in alternative embodiments, powder 160 is any powder that enables the additive manufacturing system 10 to function as described herein.

In the exemplary embodiment, structure 158 is annular and surrounds component 124. In alternative embodiments, structure may include an annular outer wall and annular inner wall, both surrounding component 124 such that component 124 is positioned between the annular outer wall and the annular inner wall. In alternative embodiments, structure 158 may be of any shape that allows it to at least partially surround component 124. In the exemplary embodiment, structure 158 has a height generally perpendicular to powder bed 138. Additionally, in further alternative embodiments, structure 158 may be oriented at any angle that allows it to function as described herein.

In the exemplary embodiment structure 158 has a density sufficient to substantially prohibit the transfer of powder 160 through structure 158 such that powder 160 is lost through the structure at a low enough rate that a recoater may compensate powder 160 lost through structure 158 to substantially powder free region 139. In other words, structure 158 may have a porous enough density such that some powder 160 passes through structure 158 as long as the rate at which powder 160 passes through structure 158 is less than the rate at which powder 160 is able to be deposited by the recoater. In the exemplary embodiment, structure 158 is separated from component 124 only by the volume of powder 160 contained by structure 158. However, in alternative embodiments, other structures may be positioned between structure 158 and component 124. For example, in alternative embodiments, an additional solid breaking wall (not shown) is positioned between structure 158 and component 124. The breaking wall increases the structural integrity of structure 158 by reducing a pressure exerted by the volume of powder 160 on structure 158. Additionally, in alternative embodiments, an open support structure (not shown) may be coupled to the powder side of structure 158. The open support structure increases the structural integrity of structure 158 by inhibiting warping of structure 158. For example, the open support structure may include a plurality of lattice structure unit cells, wherein each lattice unit cell has a lattice shape of at least one of triclinic, monoclinic, orthorhombic, tetragonal, hexagonal, cubic, and spherical. Alternatively, the open support structure includes any arrangement of unit cells that enables the open support structure to function as described herein. In further alternative embodiments, a breaking wall is positioned between structure 158 and component 124, and an open support structure is coupled to structure 158.

Figure 4:
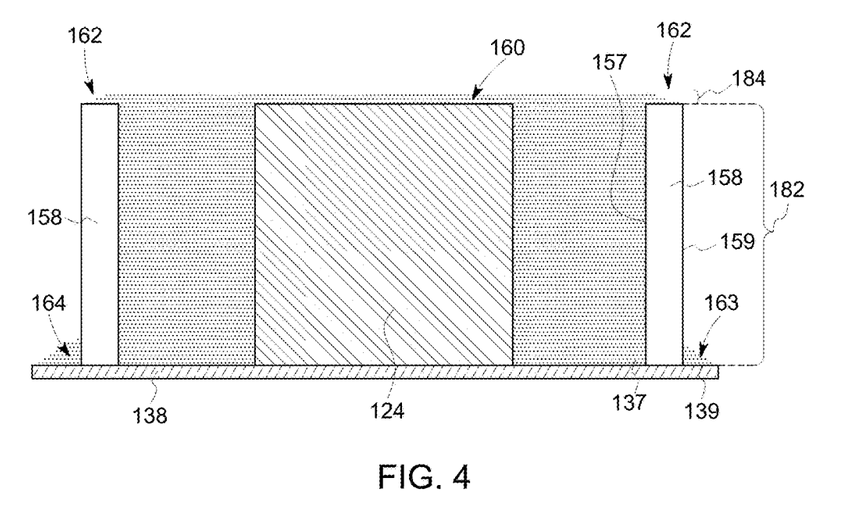
FIG. 4 is a section side schematic view of the component and structure of FIG. 3 taken along line 4-4 (as shown in FIG. 3)

FIG. 4 is a section side schematic view of the component 124 and structure 158 of FIG. 3 taken along line 4-4 (as shown in FIG. 3). In the exemplary embodiment in the state shown in FIGS. 3 and 4, component 124 and structure 158 are partially constructed midway through one build cycle. In the exemplary embodiment, component 124 is surrounded by structure 158. In alternative embodiments, structure 158 only partially surrounds the component 124. In further alternative embodiments, structure 158 includes two or more distinct wall sections which, in combination, partially surround component 124.

In the exemplary embodiment, structure 158 has a height 182 extending from powder bed 138, to a last layer of powder 160 that is consolidated on top of structure 158. In the exemplary embodiment, structure 158 has a thickness equal to the thickness of one contour scan of the laser (not shown in FIG. 4). Alternatively, structure 158 may have any thickness that enables additive manufacturing system 10 to function as described herein.

In the exemplary embodiment, powder 160 fills the volume between structure 158 and component 124. In the exemplary embodiment, powder 160 is deposited within powder bed 138 using a recoater (not shown in FIG. 4). Alternatively, powder 160 may be deposited within powder bed 138 by any other means that enables additive manufacturing system 10 to function as described herein. In the exemplary embodiment, the recoater applies a layer of powder 160 having a uniform height and spanning the area of powder bed 138 enclosed by, and including the thickness of, structure 158. In the exemplary embodiment, after the recoater applies a new layer of powder 160, powder 160 extends a layer height 184 above the height 182 of structure 158 and component 124. In the exemplary embodiment, layer height 184 is the height which powder 160 extends above the last layer of powder that was consolidated. Specifically, in the exemplary embodiment, layer height 184 is equal to the height of the most recent layer of powder 160 deposited by one pass of the recoater.

In the exemplary embodiment, the recoater applies the layer of powder 160 such that substantially no powder is spread outside of structure 158. As a result, structure 158 includes a first surface 157 bordering powder 160 and second surface 159 bordering substantially powder free region 139. Thus, in the exemplary embodiment, when the recoater applies a new layer of powder 160 extending across the thickness of structure 158, at least some portion of powder 160 spread on top of structure 158 falls into substantially powder free region 139. This lost powder 163 results in the new layer of powder 160 having a powder starved edge 162. Depending on the size of powder starved edge 162, the effect of powder starved edge 162 is that powder 160 may be consolidated unevenly. Furthermore, if this occurs over the course of several layers of manufacture, the uneven consolidation of powder 160 within structure 158 may result in defects in structure 158.

Figure 5:
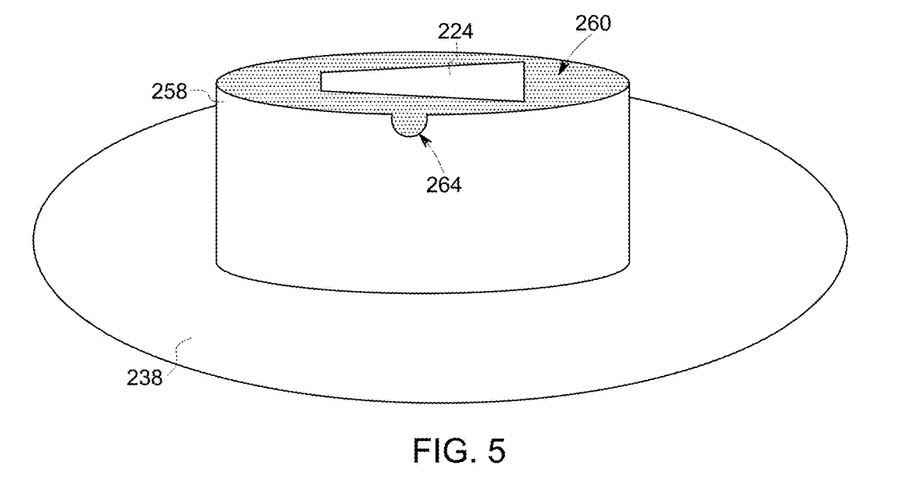
FIG. 5 is a perspective schematic view of a powder bed including structure having a defect.

FIG. 5 is a perspective schematic view of a powder bed 238 including a structure 258 having a defect 264. Specifically, in the exemplary embodiment defect 264 results from consolidating a powder 260 from a powder starved edge on structure 258. Alternatively, defect 264 may be caused by any other issue arising in the additive manufacturing process.

In the exemplary embodiment, defect 264 is a divot defined in structure 258. Alternatively, defect 264 may be a fracture or cracking of structure 258. In further alternative embodiments, defect 264 may be any discontinuity in structure 258 that permits the passage of powder 260 through the discontinuity. Additionally, in alternative embodiments including an open support structure, defect 264 may propagate through open support structure, thereby making repair of the open support structure in addition to structure 258 desirable. In the exemplary embodiment, defect 264 is located at the top of structure 258. In alternative embodiments defect 264 propagates within structure 258 and closes at a height below the top of structure 258. In further alternative embodiments, defect 264 may be positioned at any location within the structure that is capable of being reached by a consolidation device and penetrates structure 258 at least enough that additional powder 260 exists within a portion of the defect. Defect 264 may develop slowly over the course of dozens of layers. As a result, early detection of defect 264 can reduce the scope of repairs required. If left unrepaired, defect 264 may inhibit the ability of structure 258 to contain powder 260. Therefore, if left unrepaired, defect 264 may inhibit the even distribution of powder 260 within structure 258 and thereby inhibit the build process.

In the exemplary embodiment, defect 264 may be detected by a human observer monitoring the build process (e.g., by the naked eye or through a multi-monitor display displaying at least a portion of structure 258). Alternatively, defect 264 may also be detected through using an automated imaging system capable of visually detecting defect 264. For example, defect 264 may be detected through use of a camera in line sight of the structure, surface characterization of powder bed 238 using a laser line scanner, or optical images of the structure side or top surface.

In the exemplary embodiment, after defect 264 in structure 258 is detected, the repair process is initiated. In the exemplary embodiment, the repair process includes recoating the current layer of powder with a supplemental layer of powder before a supplemental scan path is commenced. In alternative embodiments however, where defect 264 is detected after powder 260 has been recoated and before the laser has been controlled to consolidate powder 260 along the first and second scan paths, recoating may not be necessary.

Figure 6:
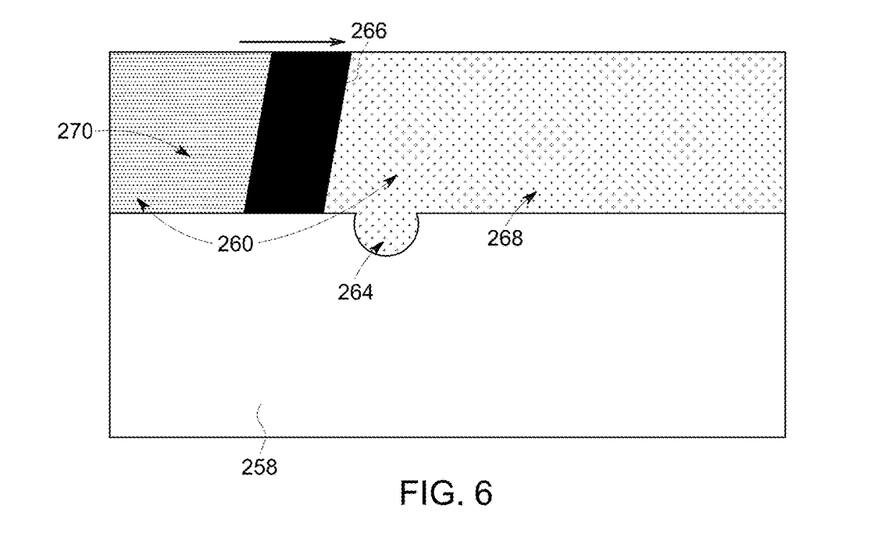
FIG. 6 is an enlarged schematic view of the structure having a defect of FIG. 5 during a recoating process.

FIG. 6 is an enlarged schematic view of structure 258 having defect 264 of FIG. 5 during a recoating process. In the exemplary embodiment, a recoater 266 traverses a first layer 268 of powder 260 and deposits a second layer 270 of powder 260 on top of first layer 268. In the exemplary embodiment, the recoating is performed to distribute powder 260 within defect 264 so that an even distribution within defect 264 is presented to a laser 272 (shown in FIG. 7) for repair. In alternative embodiments, recoating is not necessary where defect 264 is relatively minor or there already exists a uniform distribution of powder 260 within defect 264. In further alternative embodiments, recoater 266 only deposits the second layer 270 of powder 260 in the area of defect 264. In further alternative embodiments, recoater 266 is only used to redistribute the first layer 268 of powder 260 about defect 264 (i.e., without adding second layer 270). For example, in such alternative embodiments, recoater 266 may affect the displacement of powder 260 within defect 264 by applying a localized pressure to a surface normal of first layer 268 around defect 264.

In the exemplary embodiment, first layer 268 is recoated with second layer 270 after laser 272 is controlled to consolidate powder 260 along the supplemental scan path of first layer 268. In alternative embodiments, laser 272 consolidates first layer 268 along the supplemental scan path before recoater 266 applies second layer 270 on top of first layer 268.

Figure 7:
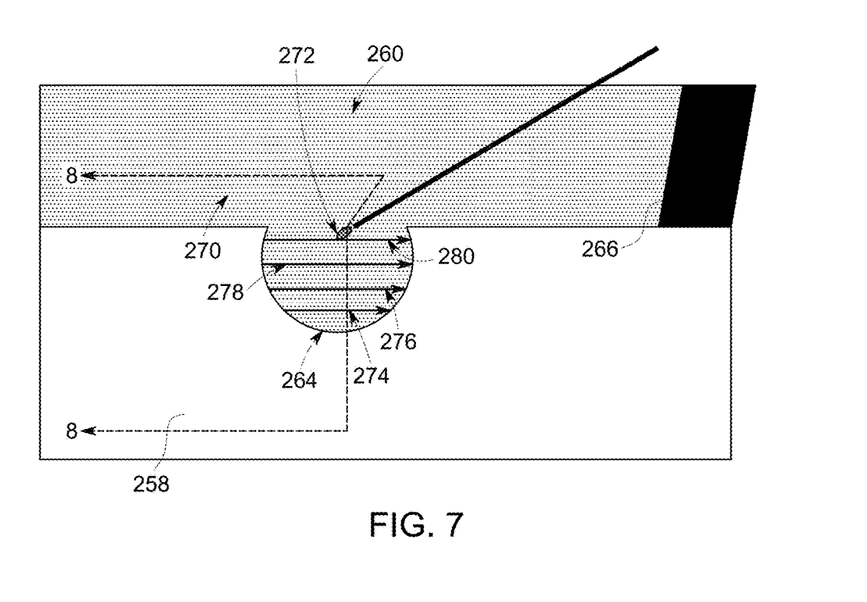
FIG. 7 is an enlarged perspective schematic view of the structure of FIG. 6 while a laser traces a supplemental scan path.

FIG. 7 is an enlarged perspective schematic view of structure 258 of FIG. 6 while laser 272 traces a supplemental scan path. As shown in the exemplary embodiment, laser 272 is controlled to trace a supplemental scan path spanning defect 264.

In the exemplary embodiment, a single laser 272 is used to consolidate powder 260 in the repair process. However, in alternative embodiments, multiple lasers are used to increase the throughput of heat transfer to the powder 260. In the exemplary embodiment, the laser 272 only consolidates powder 260 along the portion of structure 258 exposed by defect 264. However, in alternative embodiments including an open support structure coupled to the structure, and wherein defect 264 has propagated through the open support structure, laser 272 also consolidates powder 260 along a scan path relating to the portion of the open support structure in which defect 264 has propagated.

In the exemplary embodiment, the supplemental scan path is determined in reference to the portion of the second scan path associated with the location of defect 264. In the exemplary embodiment, defect 264 location information is determined by physical measurement of defect 264. For example, in the exemplary embodiment, the location of defect 264 in relation to the second scan path may be determined by physical observation by a human operator. In alternative embodiments, defect 264 location information may be determined by a spotting optic (not shown). Specifically, the spotting optic may be positioned such that it is capable of relating any observed area of second face 259 of the structure 258 to that area's corresponding coordinates in the build file or scan path data set. For example, in alternative embodiments, the spotting optic is registered to a corresponding build file or scan path data set of structure 258 such that supplemental scan path may be computed automatically. In further alternative embodiments, defect 264 location information is determined by computing the supplemental scan path based on an estimate of where defect 264 is located in relation to the second scan path. Laser 272 is then controlled to trace the supplemental scan path and an observer determines whether that path corresponds with defect 264. In the event that the supplemental scan path does not correspond with defect 264, the supplemental scan path is adjusted to compensate for the incongruity between defect 264 and the supplemental scan path. In a further alternative embodiment, defect 264 location information is determined by a combination of the spotting optic, physical measurement, and estimating techniques.

In the exemplary embodiment, once the location information of defect 264 is determined, the supplemental scan path is computed by isolating the portion of the second scan path that relates to the location of defect 264. The supplemental scan path is thereby computed to trace a contour of defect. In alternative embodiments, the supplemental scan path may be computed and executed automatically based on location information obtained about defect 264 by the spotting optic.

In the exemplary embodiment, the supplemental scan path includes a plurality of independently executable scans, each scan of the plurality of independently executable scans configured to traverse a contour of defect 264. Specifically, in the exemplary embodiment, supplemental scan path includes a first scan 274, a second scan 276, a third scan 278, and a fourth scan 280. In alternative embodiments, supplemental scan path includes only one scan configured to traverse the contour of defect 264. In further alternative embodiments, supplemental scan path includes as many scans as is necessary to repair defect 264. Additionally, in the exemplary embodiment, an operator determines the state of defect 264 after each scan of the supplemental scan path. If defect 264 is still observed, controller 34 controls laser 272 to execute an additional scan of the supplemental scan path based on location information of defect 264 gathered after the previous scan. If the defect is cured, the controller 34 controls the laser 272 to return to executing the first and second scan paths of the build file or scan path data set. In alternative embodiments, the state of defect 264 after each scan may be determined automatically through the use of at least one imaging sensor.

In the exemplary embodiment, each scan of the plurality of independently executable scans traverses the contour of defect 264 in the same direction. In alternative embodiments, each scan of the plurality of independently executable scans is oriented in a direction opposite to the previous scan.

In the exemplary embodiment, there is no Z movement of powder bed 238 in between the scan and recoat cycles of the supplemental scan path. Instead, controller 34 controls actuator system 36 to position powder bed 238 at a constant vertical height while the supplemental scan path is executed. Additionally, in alternative embodiments, controller 34 controls scanning motor to affect scanning mirror 20 to adjust the focus of laser 272 to correspond with varying heights of the independently executable scans of the supplemental scan path.

Figure 8:
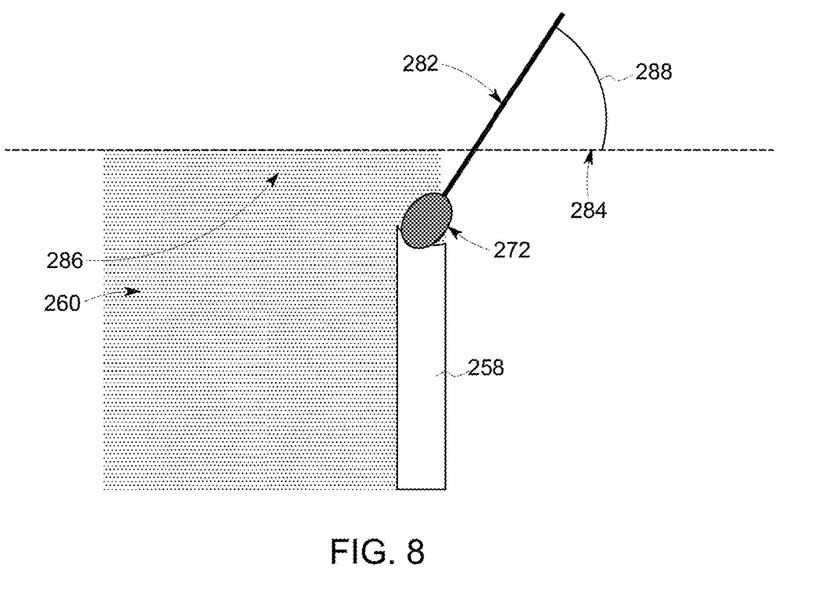
FIG. 8 is an enlarged section side schematic view of the structure of FIG. 7 taken along line 8-8 (as shown in FIG. 7)

FIG. 8 is an enlarged section side schematic view of the structure of FIG. 7 taken along line 8-8 (as shown in FIG. 7). In the exemplary embodiment, a trajectory 282 of laser 272 is oriented such that intersection of a plane 284 substantially parallel to a top surface 286 of powder 260 and trajectory 282 form an acute angle 288 at their intersection. However, in alternative embodiments, trajectory 282 is oriented such that angle 288 is a right angle.

FIG. 9A through 9D are images showing respective first, second, third, and fourth times during a repair of a structure.

Figure 9A:
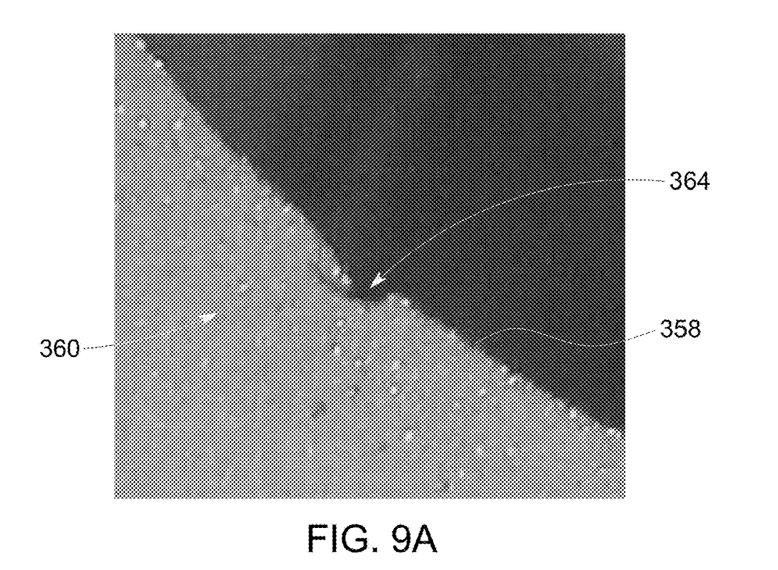
FIG. 9A through 9D are images showing respective first, second, third, and fourth times during a repair of a structure.

FIG. 9A shows an aerial view of a first time during the repair of structure 358. At the first time, a defect 364 is identified. In the exemplary embodiment, defect 364 is detected while the laser (not shown in FIG. 9) is being controlled to trace the first and second scan paths of the build file or scan path data set. In the exemplary embodiment, once defect 364 is identified, the controller controls the laser to adjust to trace a supplemental scan path. In alternative embodiments, defect 364 may be detected during recoating. In such embodiments, once defect 364 is identified, the controller may either control the recoater to temporarily stop recoating and control the laser to trace a supplemental scan path, or the controller may control the recoater to finish recoating the top layer of powder 360 and then control the laser to trace the supplemental scan path. In further alternative embodiments, defect 364 may be after laser tracing and before recoating. In the further alternative embodiments, once defect 364 is identified, the controller may either control the laser to begin tracing a supplemental scan path or the controller may control the recoater to first recoat a top layer of powder 360 and then control the laser to begin tracing the supplemental scan path.

In the exemplary embodiment, defect 364 breaches structure 358. Alternatively, defect 364 may be a light fracture or cracking of structure 358. In the exemplary embodiment, defect 364 is located at the top of structure 358. In alternative embodiments defect 364 may propagate within structure 358 at a height below the top of structure 358. In further alternative embodiments, defect 364 may be positioned at any location within the structure that is capable of being reached by a consolidation device and penetrates structure 358 at least enough that additional powder 360 exists within a portion of the defect. Defect 364 may develop slowly over the course of dozens of layers.

Figure 9B:
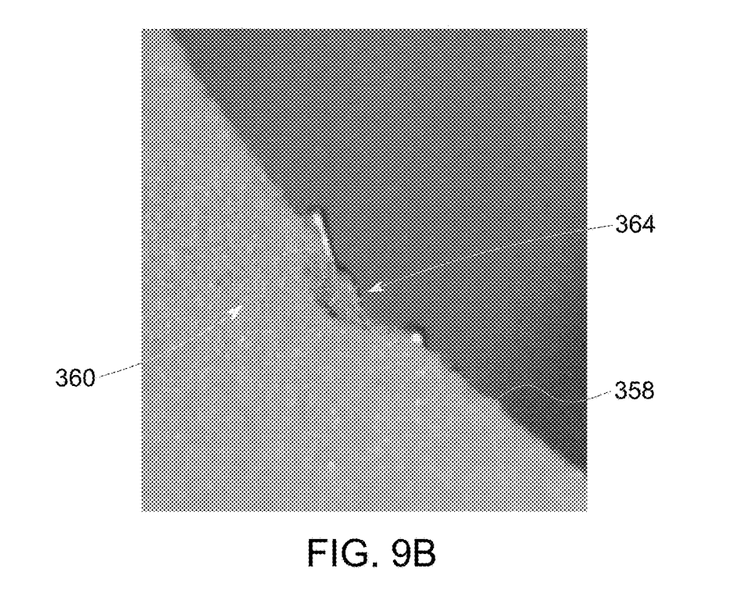

FIG. 9B shows an image at a second time during the repair of structure 358. The second time is subsequent to the first time. At the second time, structure repair process is being carried out. Specifically, at the second time, the laser (not shown) is used to consolidate powder 360 exposed within defect 364 along a supplemental scan path. In the exemplary embodiment, structure 358 has a thickness equal to that of the contour of the laser. Alternatively, structure 358 may have any suitable thickness. In the exemplary embodiment, at the second time, a first scan of the supplemental scan path has occurred but defect 364 is still detectable. Thus, in the exemplary embodiment, multiple scans of the supplemental scan path are necessary to repair structure 358. In alternative embodiments, one scan of the supplemental scan path may be sufficient to repair defect 364.

Figure 9C:
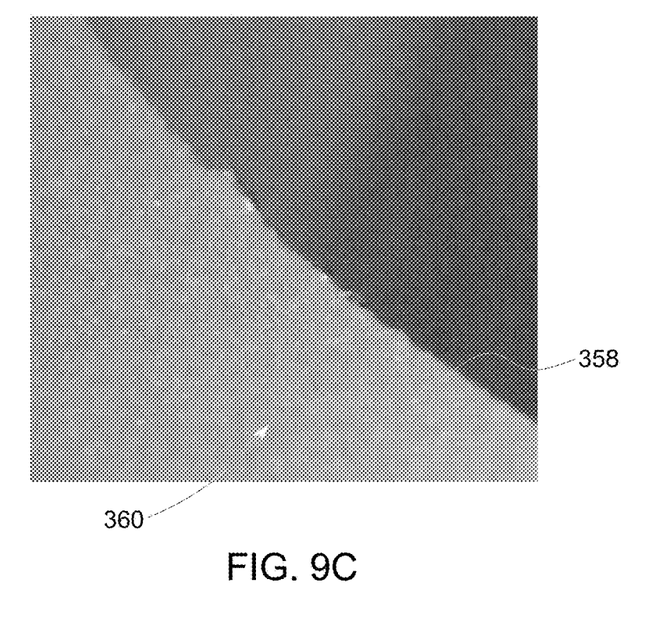

FIG. 9C shows an image at a third time during the repair of structure 358. The third time is subsequent to the second time. At the third time, defect 364 is no longer detected. Thus, the laser is controlled to resume the first and second scan paths of the build file or scan path data set.

Figure 9D:
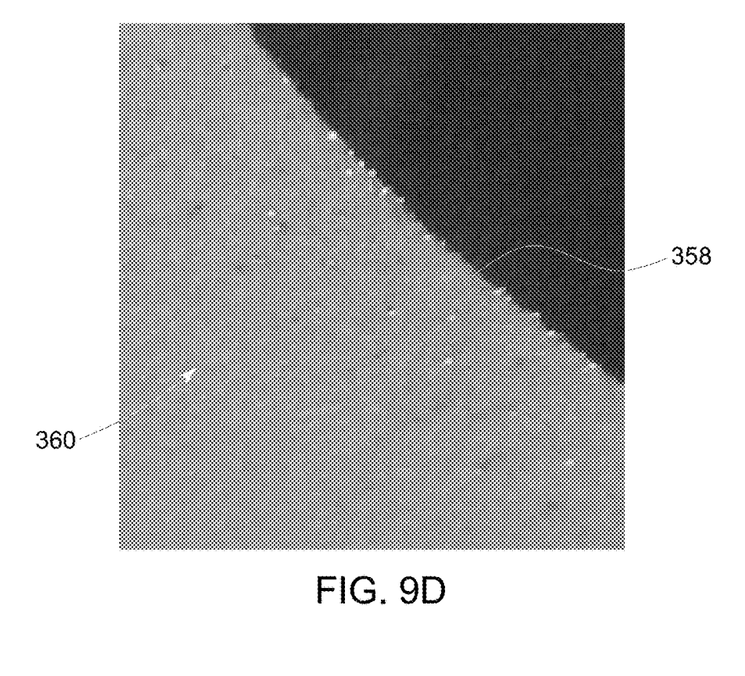

FIG. 9D shows an image at a fourth time during the repair of structure 358. The fourth time is subsequent to the third time. At the fourth time, the build process of additive manufacturing system 10 has been resumed.

Figure 10:
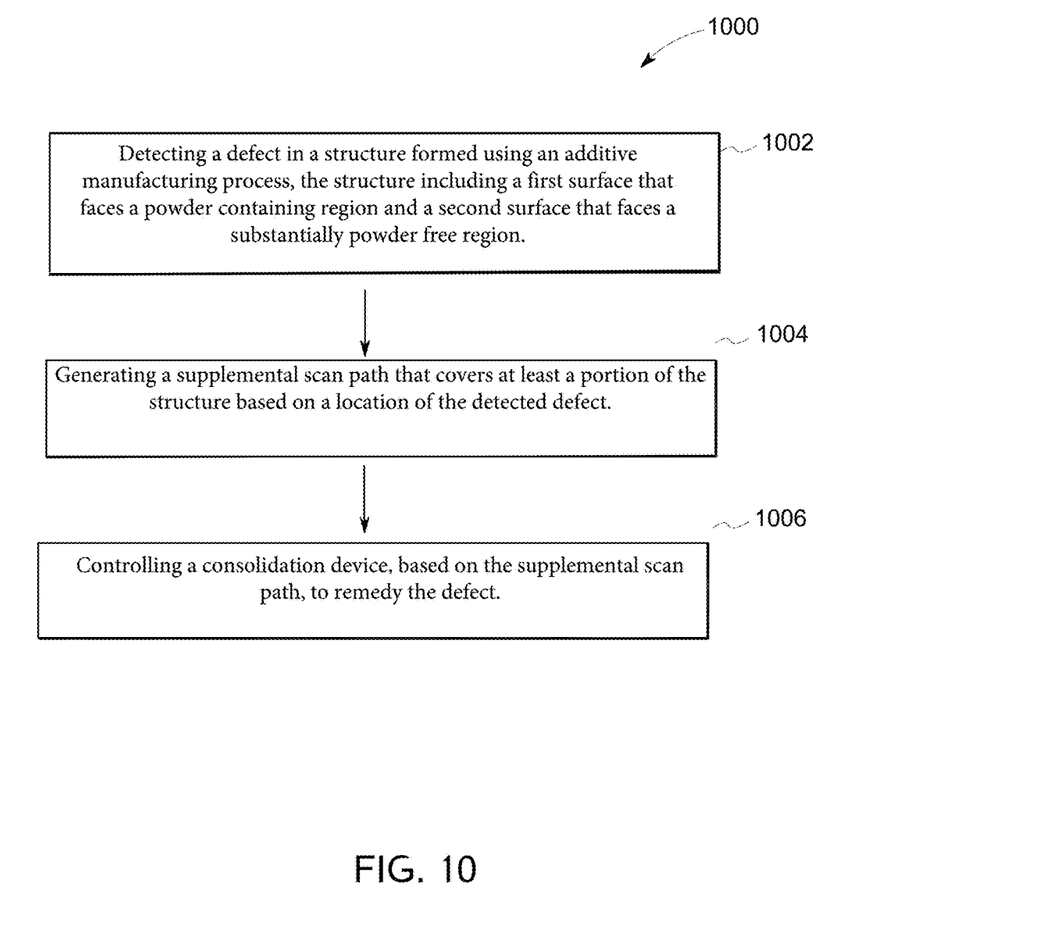
FIG. 10 is a flowchart of an exemplary method that may be used to repair a structure.

FIG. 10 is a flowchart of an exemplary method 1000 that may be used to repair a structure. Referring to FIGS. 1-8, method 1000 includes detecting 1002 a defect in a structure formed using an additive manufacturing process, the structure including a first surface that faces a powder containing region and a second surface that faces a substantially powder free region.

In the exemplary embodiment, method also includes generating 1004 a supplemental scan path that covers at least a portion of the structure based on a location of the detected defect.

Finally, in the exemplary embodiment, method 1000 includes controlling 1006 a consolidation device, based on the supplemental scan path, to remedy the defect.

Exemplary embodiments of methods and systems for repairing powder containment walls are described above in detail. The repair methods and systems are not limited to the specific embodiments described herein, but rather, components of systems and/or steps of the methods may be utilized independently and separately from other components and/or steps described herein. For example, the methods may also be used in combination with other additive manufacturing systems, and are not limited to practice with only SLM systems, and methods as described herein.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:
1. An additive manufacturing method comprising:
   detecting a defect in a structure formed using an additive manufacturing process, the structure including a first surface that faces a powder containing region and a second surface that faces a substantially powder free region;

generating a supplemental scan path that covers at least a portion of the structure based on a location of the detected defect; and controlling a consolidation device, based on the supplemental scan path, to remedy the defect.

2. The additive manufacturing method of claim 1 further comprising:

receiving a first scan path for a component and a second scan path for the structure;

controlling the consolidation device, to consolidate the powder along the first and second scan paths to form the component and the structure in the same build cycle, wherein the structure at least partially surrounds the component; and resuming the first scan path and the second scan path after remedying the defect.

3. The additive manufacturing method of claim 2 further comprising:

placing a first layer of the powder within at least a portion of a powder bed; and recoating a first layer of the powder within the defect to create a second layer of the powder within the defect.

4. The additive manufacturing method of claim 2 further comprising:

recoating the defect prior to controlling the consolidation device to remedy the defect.

5. The additive manufacturing method of claim 2 further comprising:

determining the supplemental scan path based on the second scan path and the location of the defect.

6. The additive manufacturing method of claim 1, wherein the defect is a discontinuity in the structure that permits the passage of powder through the structure.

7. The additive manufacturing method of claim 1, wherein the structure is a powder containment wall at least partially surrounding a component.

8. The additive manufacturing method of claim 1, wherein the structure is a component manufactured in an additive manufacturing process.

9. The additive manufacturing method of claim 1, wherein the supplemental scan path includes a plurality of scans.

10. The additive manufacturing method of claim 9, wherein the supplemental scan path includes a first scan that traverses a contour of the defect.

11. The additive manufacturing method of claim 10 further comprising:

executing a second scan of the supplemental scan path based on a subsequent detection of the defect after the first scan.

12. An additive manufacturing system comprising:
a consolidation device;
a powder bed; and
a controller comprising a processing device and a memory device, said controller configured to:
generate a supplemental scan path based on a location of a detected defect in a structure formed using an additive manufacturing process, the structure including a first surface that faces a powder containing region and a second surface that faces a substantially powder free region; and
control said consolidation device, based on the supplemental scan path, to remedy the defect.

13. The additive manufacturing system of claim 12, wherein said controller is further configured to:

receive a first scan path for a component and second scan path for a structure;

control said consolidation device, to consolidate a powder in said powder bed along the first and second scan paths to form a component and the structure in the same build cycle, wherein the structure at least partially surrounds the component; and control said consolidation device to resume the first scan path and the second scan path after remedying the defect.

14. The additive manufacturing system of claim 12, wherein the defect is a discontinuity in the structure that permits the passage of powder through the structure.

15. The additive manufacturing system of claim 12, wherein the structure is a powder containment wall at least partially surrounding a component.

16. The additive manufacturing system of claim 12, wherein the structure is a component to be manufactured in the additive manufacturing process.

17. The additive manufacturing system of claim 12 further comprising:

an actuator configured to move said powder bed; and
a recoater configured to distribute powder in said powder bed.

18. A controller for controlling an additive manufacturing system comprising:
a memory device;
a user input interface; and
a processing device, said processing device configured to:
generate a supplemental scan path based on a location of a detected defect in a structure formed using an additive manufacturing process, the structure including a first surface that faces a powder containing region and a second surface that faces a substantially powder free region; and
control a consolidation device, based on the supplemental scan path, to remedy said defect.

19. The controller of claim 18 further configured to:
receive a first scan path for a component and second scan path for the structure;
control said consolidation device, to consolidate a powder in a powder bed along the first and second scan paths to form a component and the structure in the same build cycle, wherein the structure at least partially surrounds said component; and
control the consolidation device to resume the first scan path and the second scan path after remedying the defect.

20. The controller of claim 18, wherein the controller is further configured to control a recoater to recoat the defect.

* * * * *